United States Patent [19]
Storz

[11] Patent Number: 5,529,570
[45] Date of Patent: Jun. 25, 1996

[54] LARYNGOSCOPIC SPATULA

[76] Inventor: Karl Storz, Auf dem Schildrain 39, D-78532 Tuttlingen, Germany

[21] Appl. No.: 114,071

[22] Filed: Aug. 30, 1993

[30] Foreign Application Priority Data

Sep. 5, 1992 [DE] Germany .......................... 42 29 739.7
Dec. 23, 1992 [DE] Germany .......................... 42 43 790.3

[51] Int. Cl.$^6$ ............................................. A61B 1/06
[52] U.S. Cl. ..................... 600/199; 600/185; 600/188; 600/194
[58] Field of Search ................................. 128/10, 11, 17, 128/18, 4, 12, 13, 14, 15, 16; 600/185, 188, 194, 199

[56] References Cited

U.S. PATENT DOCUMENTS

| | | | |
|---|---|---|---|
| 3,595,222 | 7/1971 | Vellacott | 128/11 |
| 4,556,052 | 12/1985 | Müller | 128/11 |
| 4,565,187 | 1/1986 | Soloway | |
| 4,570,614 | 2/1986 | Bauman | 128/11 |
| 4,592,343 | 6/1986 | Upsher | 128/11 |
| 5,060,633 | 10/1991 | Gibson | 128/11 |

FOREIGN PATENT DOCUMENTS

| | | |
|---|---|---|
| 0339541 | 4/1989 | European Pat. Off. . |
| 8526662.0 | 9/1985 | Germany . |

Primary Examiner—Richard J. Apley
Assistant Examiner—Beverly M. Flanagan
Attorney, Agent, or Firm—Donald D. Mon

[57] ABSTRACT

A laryngoscopic spatula comprises a handle, a spatula-shaped portion and a light pipe (2) containing glass fibers, through which light rays emitted by a light source can be guided via the glass fibers. For enabling the light pipe (2) to be easily exchanged it is provided that the light pipe (2) is configured as a detachable part, that the spatula-shaped portion (10) is provided with a recess adapted for receiving at least an area of the light pipe (2), and that the light pipe is fixed in the recess in its final position. (FIG. 9).

7 Claims, 4 Drawing Sheets

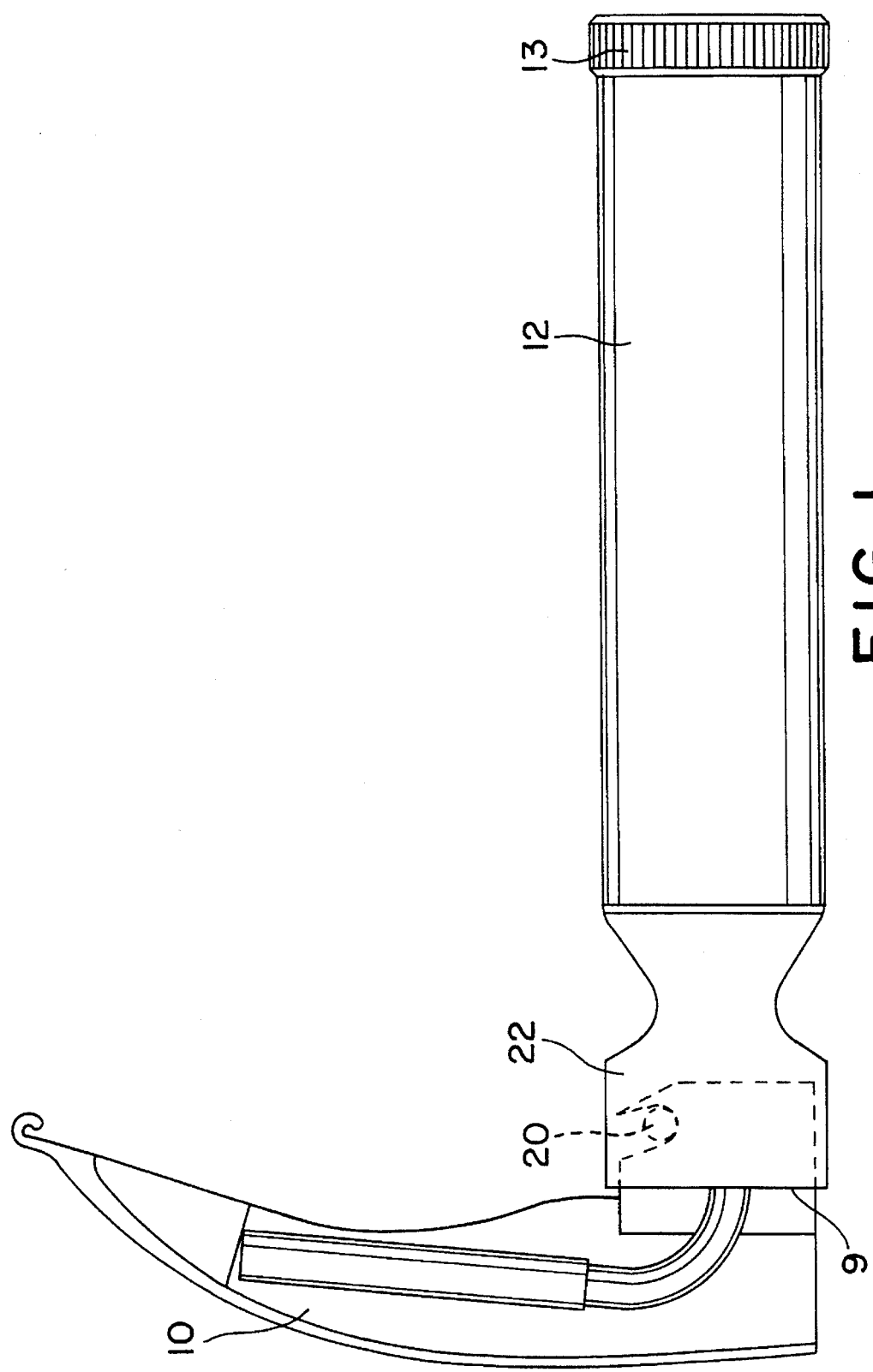

LARYNGOSCOPIC SPATULA

The present invention relates to a laryngoscopic spatula, in particular for introducing anesthetic tubes into the trachea, having a handle, a spatula-shaped portion and a light pipe containing glass fibers, through which light rays emitted by a light source can be guided via the glass fibers.

Among the group of laryngoscopic spatulae for introducing anesthetic tubes into the trachea, preference is given to those embodiments where the light rays are guided via glass fibers. However, these embodiments are connected with the disadvantage that when the fiberoptic properties of the glass fibers have deteriorated by extended use, they can be replaced only with considerable technical effort and expense, if at all.

There have also been known laryngoscopic spatulae where the electric current is guided from the handle into the spatula-shaped portion via a mechanical coupling, and via an electric line to a bulb located at the proximal end of the spatula. Such a laryngoscopic spatula has been previously known from Karl Storz GmbH, Tuttlingen, Germany, under the product designations 8540 D and 8544.

DE-PS 32 17 476 describes a laryngoscope whose tube exhibits on its proximal end a substantially circular cross-section, in perpendicular direction to its longitudinal axis, and which is likewise provided with a handle element. The tube is subdivided in its longitudinal direction into two parts, i.e. an upper and a lower spatula-shaped part, that can be turned relative to each other about an upper axis of rotation. The respective spatula-shaped portion is intended to receive a band-shaped light pipe that can be fitted in a strap via two plug-in connections.

Now, it is the object of the present invention to improve a laryngoscopic spatula of the before-mentioned type in such a way that the light pipe can be exchanged easily and rapidly.

The invention achieves this object by the fact that the light pipe is configured as a detachable part, that the spatula-shaped portion is provided with a recess adapted for receiving at least an area of the light pipe, and that the light pipe is fixed in the recess in its final position.

It is thus possible to exchange the light pipe quickly and easily, without great technical input. This enables maintenance and cleaning work on the laryngoscopic spatula, as well as replacements of the light pipe together with the glass fibers contained therein, to be carried out easily and rapidly. By fixing the light pipe in the recess in its final position, it is ensured that the light pipe is retained on the laryngoscopic spatula for use in an undetachable way and in fixed location. By providing the recess, the light pipe can be mounted rapidly and easily in its correct position on the laryngoscopic spatula, by simply inserting it into the recess and fixing it therein. The reverse procedure, i.e. removing the light pipe after it has been released from its fixed position, is also effected rapidly and easily by simply lifting the light pipe off the recess.

The light pipe may be fixed in the recess by mechanical means, for example by snap-in connections, screw connections or a bayonet joint.

It is also envisaged to make use of a magnetic effect for fixing purposes, in which case the light pipe, being produced from a metallic material, is fixed in the recess by the effect of a magnet.

According to a particularly advantageous embodiment of the invention, the light pipe is introduced laterally into a first position in the light pipe from where it can be moved to its final position by a pivotal movement, by which it is simultaneously fixed in position.

According to another advantageous embodiment of the invention, the light pipe is expanded on its light-source end, and in the final position of the light pipe the expanded end engages an expanded area of the recess.

This feature provides the advantage that in a first step the light pipe can be introduced by an area of reduced cross-section into an area of the recess of correspondingly reduced cross-section, whereafter the expanded end is introduced into the expanded area of the recess, for example by a pivotal movement of the light pipe. Specifically, the expanded area may be guided by a thread or a bayonet guide, and can thus be moved securely and simply into its predetermined position on the laryngoscopic spatula, while the light pipe is simultaneously fixed in position. That is, once the light pipe has been turned into its final position, the expanded end of the light pipe can no longer be removed laterally from the expanded area of the recess so that any unwanted detaching of the light pipe from the laryngoscopic spatula is excluded.

Other features of the invention are specified in the sub-claims.

Other advantages and details of the invention will become apparent from the following description of two embodiments of the invention and the attached drawings in which:

FIG. 1 shows a side view of a first embodiment of the invention;

Figure 4:
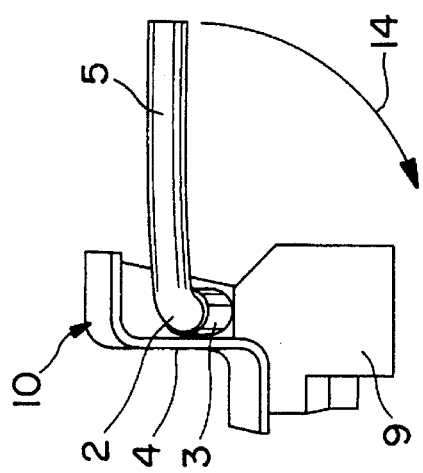
FIG. 4 shows a rear view of the spatula-shaped portion according to FIG. 3.

A laryngoscopic spatula as illustrated in FIG. 1 comprises a handle 12, which is closed on its end by a screw cap 13.

Inside the handle 12, a battery and a miniature bulb acting as a light source are arranged in the known manner, i.e. adjacent to glass fibers leading into a light pipe 2. The light pipe 2 consists of a metal tube with glass fibers contained therein. Thus, the glass fibers specifically described herein serve as fiberoptic waveguide. This method of light transmission is known as such from the prior art so that its details need not be explained and illustrated herein more explicitly.

On the end opposite the screw cap 13, one can see a coupling 9 by means of which a spatula-shaped portion 10 can be coupled to the handle 12, as will be explained hereafter in more detail. The coupling 9 serves as a mounting 7 for retaining the spatula-shaped portion 10 on the handle 12.

This sort of coupling between the spatula-shaped portion 10 and the handle 12 is also known from the prior art so that it need not be explained here in more detail.

Figure 2:
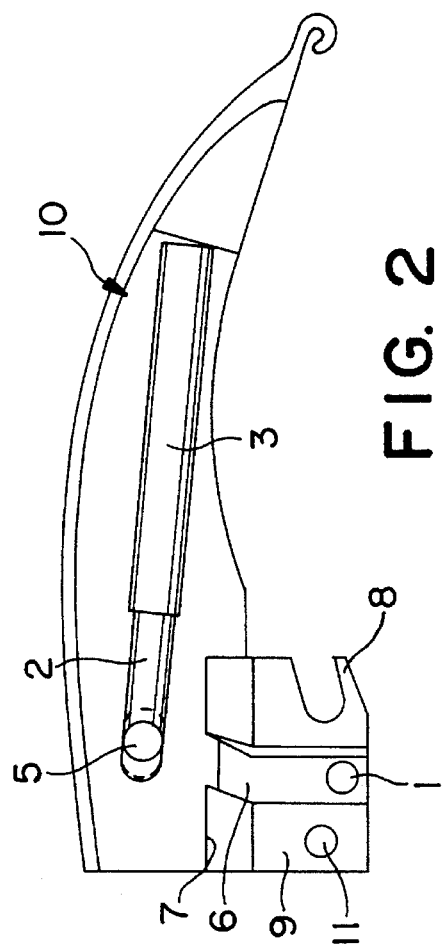
FIG. 2 shows a side view of only the spatula-shaped portion after it has been uncoupled from the handle.

Referring now to FIG. 2, it can be seen that the coupling 9 comprises a coupling hook 8 engaging a pin 20 of the handle 12 which is indicated by broken lines in FIG. 1.

FIG. 2 further shows a lateral spring-loaded coupling pin 11 which, when the handle 12 is clicked into place, engages a corresponding inner recess provided on a portion 22 of the handle 12 that projects laterally in longitudinal direction. On the opposite side of the coupling 9, there is provided another similar spring-loaded coupling pin which engages a corresponding recess in an oppositely arranged, laterally projecting portion of the handle 12.

As can be seen particularly clearly in FIG. 1, the end portion of the coupling 9 is trapped in coupled condition between the two laterally projecting portions 22 of the handle 12. The pin 20, which is engaged by the coupling hook 8, extends between these two portions 22.

As can be further seen in FIG. 2, a lateral recess 6 is provided in an area between the coupling hook 8 and the spring-loaded coupling hook 11, for engagement by a bent-off portion 5 of the light pipe 2.

In the representation of FIG. 2, however, the bent-off area 5 is swung out laterally from the recess 6. This is also clearly visible in FIGS. 3 and 4.

Figure 3:
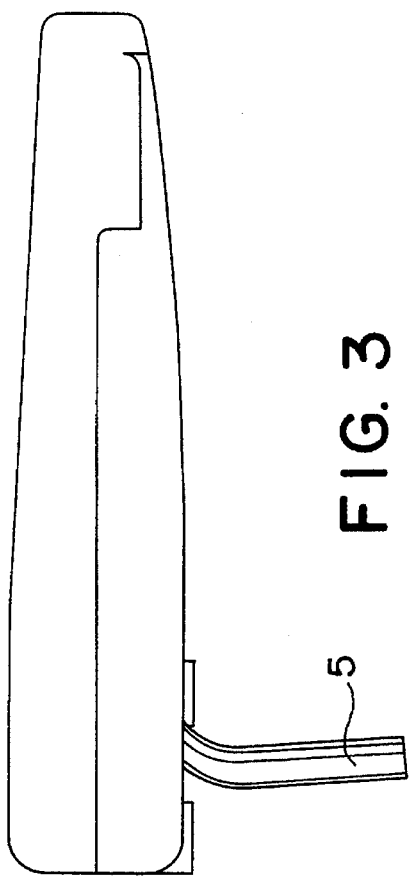
FIG. 3 shows a top view of the spatula-shaped portion according to FIG. 2, with the light pipe in laterally swung-out position.

As is further apparent from FIG. 2, the end portion of the light pipe 2, on its light-emitting side, is fitted in a tubular piece 3 which penetrates through a vertical wall 4 of the spatula-shaped portion 10. In FIGS. 3 and 4 it can be seen that the bent-off portion 5 of the light pipe 2 is swung out laterally from the recess 6, which means that the light pipe 2 can be turned in the tubular piece 3.

Referring to FIG. 4, this possibility to turn the light pipe is indicated by an arrow 14.

It appears, especially from FIG. 2, that the light pipe 2 is introduced into the tubular piece 3, or retracted from the tubular piece 3 for replacement, by a straight movement. For ease of handling, the light pipe 2 can be easily gripped by its bent-off portion 5 in its swung-out condition illustrated in FIGS. 2 to 4. This can be done with the bare hand, i.e. without any special tools.

Figure 7:
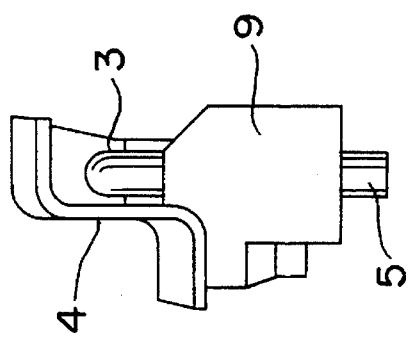
FIG. 7 shows a rear view of the representation according to FIGS. 5 and 6.
Figure 5:
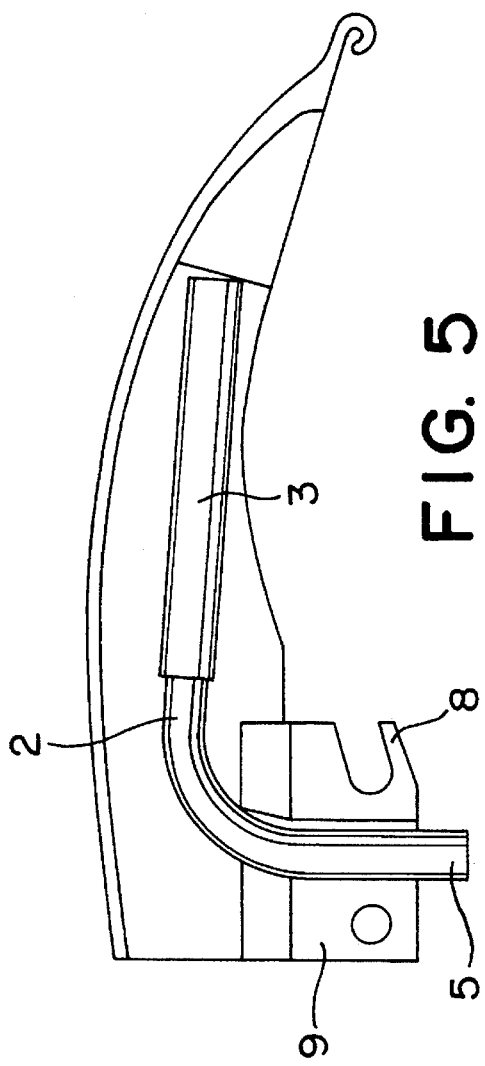
FIG. 5 shows as side view of the spatula-shaped portion according to FIG. 2, but with the light pipe in its retracted position.
Figure 6:
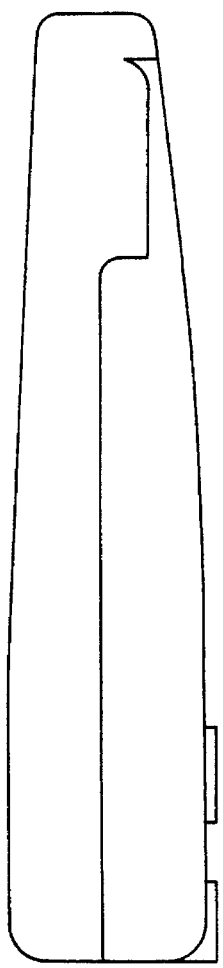
FIG. 6 shows a top view according to FIG. 3 of the representation of FIG. 5.

FIGS. 5 to 7 show the light pipe 2 in its final position, which means that the light pipe 2 has been turned until the bent-off end 5 has entered the recess 6.

From FIG. 2 it can be taken that the recess 6 accommodates a magnet 1 which fixes the light pipe 2 in the position shown in FIG. 5. Further, it can be taken from the representation of FIG. 1 that, once the spatula-shaped portion 10 is coupled to the handle 12, turning of the light pipe 2 is additionally prevented by the laterally overlapping portions 22 of the handle 12.

It is also possible to provide further magnets, in addition to the magnet 1, for the purpose of fixing the light pipe 2.

As can be seen best in FIG. 7, the bent-off portion 5 of the light pipe 2 projects a short way beyond the coupling 9. For exchanging the light pipe 2, the latter only has to be turned out from the recess 6, against the force of attraction of the magnet 1, whereafter it can be simply pulled off the tubular piece 3, for example to the left in the representation of FIG. 2.

Figure 8:
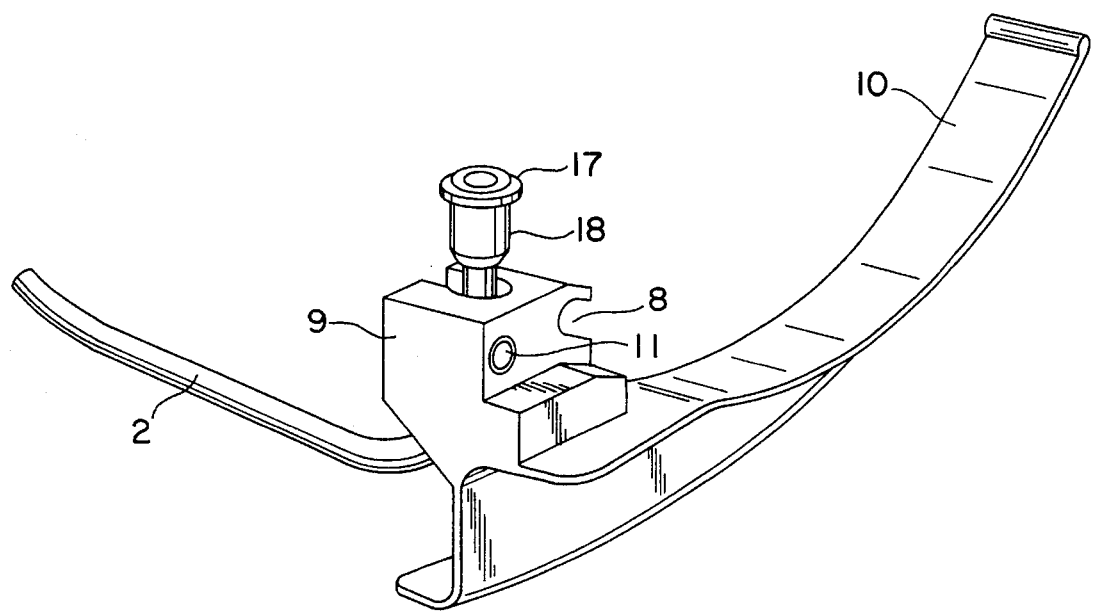
FIG. 8 shows a perspective view of another embodiment of a spatula-shaped portion, with the light pipe in swung-out position.
Figure 9:
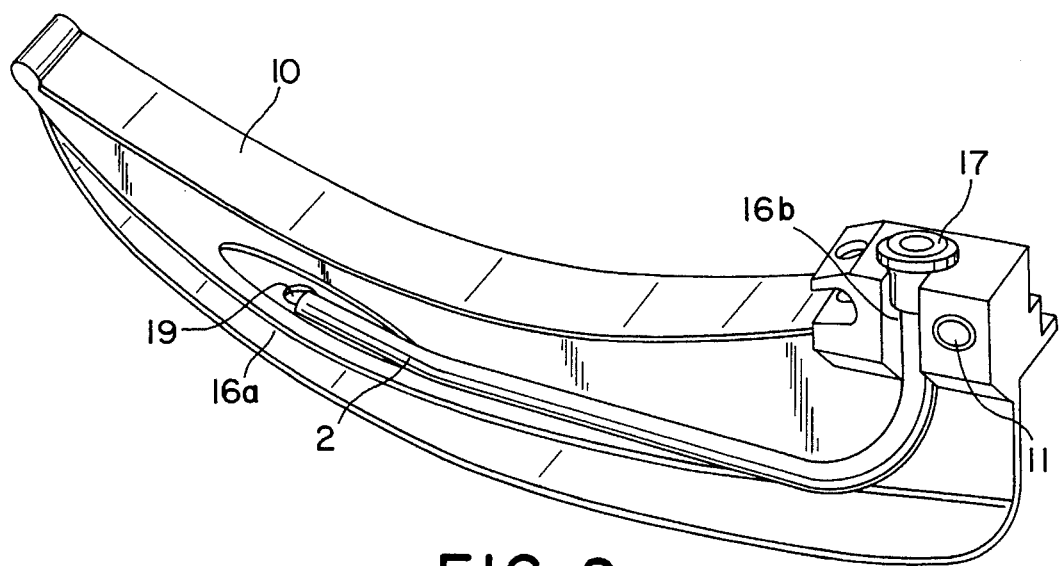
FIG. 9 shows another perspective view of the embodiment according to FIG. 8, with the light pipe in its final position.

FIGS. 8 and 9 show another embodiment of the invention, which is provided with mechanical fixing means for the light pipe 2. FIG. 8 shows again a representation with the light pipe 2 in swung-out position.

The light pipe 2 is provided for this purpose, on its end adjacent the light source, with a tubular flange 17 followed by a thread 18. The thread may also be part of a bayonet joint.

From FIG. 8 it can be taken that in the swung-out position illustrated in FIG. 8 that end of the light pipe 2 which carries the tubular flange 17 and the thread 18 can be lifted until the tubular flange 17 and the thread 18 have emerged from the recess 6. The lateral opening, or the lateral expansion 16b of the recess 6 is large enough to enable the light pipe 2 to be pulled off laterally (to the left in the representation of FIG. 8) in this position. Correspondingly, when the light pipe 2 has to be exchanged, the new light pipe can be attached or inserted in reverse direction. In order to move the light pipe 2 into its final position illustrated in FIG. 9, it is only necessary to turn it by approximately 90° which additionally causes it to nestle into another lateral expansion 16a provided on the front end portion of the spatula-shaped part 10. Flange 17 provides an expanded area on light pipe 2 at its light source end. The portion of the light pipe adjacent to flange 17 has a smaller diameter than the flange. It can pass through lateral expansion 16b (in effect a narrow slot) but the flange cannot. When the light pipe is installed, thread 18 will project above the recess so that it can be engaged by mating threads.

In this final position, the light pipe 2 is either clamped or mechanically screwed in place, without any need for additional parts, such as a screw. Rather, turning the light pipe 2 by the before-mentioned approximately 90° suffices to screw the thread 18 into the recess in the coupling 9. Alternatively, it would also be possible to provide a bayonet joint and a corresponding bayonet guide for this purpose.

From FIG. 9 it can be further derived that the front end portion of the spatula-shaped part 10 is provided with an opening 19 which is engaged by the light-emitting end of the light pipe 2.

The invention is not limited to the illustrated embodiments of the invention. The man skilled in the art has the means to implement additional embodiments within the scope defined by the claims. Specifically, the invention may also be applied for exchanging the light pipe 2 of other medical equipment in the manner specified by the invention.

I claim:

1. Laryngoscopic spatula, in particular for introducing anesthetic tubes into the trachea, having a handle, a spatula-shaped portion, a light source, and a light pipe having a light source end and a light-emitting end containing glass fibers, through which glass fibers light rays emitted by said light source can be guided via the glass fibers, wherein said light pipe is configured as a detachable part, said light pipe being provided with an expanded area at said light-source end, said spatula-shaped portion being provided with a recess adapted for receiving said expanded area of said light pipe, said recess being provided with a lateral opening having a width corresponding to the outer diameter of the light pipe in a non-expanded area, thereby allowing a lateral insertion of the light pipe into the recess through said lateral opening only by a non-expanded area thereof, wherein, in a final position of said light pipe, said expanded area of said light pipe engages a correspondingly expanded area of said recess, whereby said detachable light pipe is fixed in said recess in its final position and removable laterally through said lateral opening only when the expanded area is out of the recess.

2. Laryngoscopic spatula according to claim 1, wherein said recess is provided in an area for mounting of the spatula-shaped portion to said handle, said mounting serving to connect said spatula-shaped portion to said handle.

3. Laryngoscopic spatula according to claim 1, wherein said detachable light pipe is provided with a tubular flange in an area of its coupling to the light source.

4. Laryngoscopic spatula according to claim 1, wherein said spatula-shaped portion is provided with an opening, a light-emitting end of said detachable light pipe passing through said opening.

5. Laryngoscopic spatula according to 1, wherein said light pipe is expanded on its light-source end, and wherein, in a final position of said light pipe, said expanded end of said light pipe engages a correspondingly expanded area of said recess.

6. Laryngoscopic spatula according to claim 5 in which engagement of said light pipe in said recess is by means of a bayonet joinder.

7. Laryngoscopic spatula according to claim 5 in which engagement of said light pipe in said recess is by means of a threaded joinder.

* * * * *